United States Patent
Van Herk et al.

(10) Patent No.: US 6,301,500 B1
(45) Date of Patent: Oct. 9, 2001

(54) ELECTRO-STIMULATION APPARATUS USING ELECTRODE MATRIX AND A COUNTER ELECTRODE

(75) Inventors: Johannes J. Van Herk, Eindhoven (NL); Nigel D. Young, Redhill (GB)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/291,431

(22) Filed: Apr. 13, 1999

(30) Foreign Application Priority Data

Apr. 14, 1998 (EP) .................................................. 98302874

(51) Int. Cl.[7] ................................ A61N 1/08; A61N 1/04
(52) U.S. Cl. ............................... 607/2; 607/148; 607/152; 600/393; 600/547
(58) Field of Search ............................... 607/2, 148, 152; 600/372, 382, 393, 547, 548

(56) References Cited

U.S. PATENT DOCUMENTS

| | | | |
|---|---|---|---|
| 4,649,932 | * 3/1987 | Smith | 600/547 |
| 4,781,798 | * 11/1988 | Gough | 205/783 |
| 5,598,848 | * 2/1997 | Swanson et al. | 600/508 |
| 5,807,251 | * 9/1998 | Wang et al. | 600/407 |

FOREIGN PATENT DOCUMENTS

| | | |
|---|---|---|
| 0784960A1 | 7/1997 | (EP) . |
| 1219086A | 3/1986 | (RU) . |

* cited by examiner

Primary Examiner—Carl Layno
(74) Attorney, Agent, or Firm—Ernestine C. Bartlett; Bernard Franzblau

(57) ABSTRACT

An electro-stimulation apparatus comprises an electrode system for measuring local electrical impedance. The electrode system includes a multitude of electrode pads and a counter electrode held at a reference voltage. The electrode pads and the counter electrode are assembled in an electrode unit. A particular embodiment of the electro-stimulation apparatus comprises an electronic circuit including a source group of electrode pads and a sink group of electrode pads and a source conductor for applying a first electrical quantity to electrode pads of the source group. The electronic circuit also includes a sink conductor for receiving a second electrical quantity from electrode pads of the sink group. Switching elements couple individual electrode pads of the source group to the source conductor. Other switching elements couple individual electrode pads of the sink group to the sink conductor.

22 Claims, 5 Drawing Sheets

ELECTRO-STIMULATION APPARATUS USING ELECTRODE MATRIX AND A COUNTER ELECTRODE

BACKGROUND OF THE INVENTION

This invention relates to an electro-stimulation apparatus, comprising
- an electrode system for measuring local electrical impedance including
- a multitude of electrode pads and
- a counter electrode held at a reference voltage.

Such an electro-stimulation apparatus is for instance used in the fields of electro-acupuncture and transcutale electronic nerve stimulation (TENS). In both electro-acupuncture and TENS electrical signals are locally applied to the body of a human so as to excite particular parts of the nervous system. In particular a small electrical current is locally applied to the skin of the person undergoing electro-stimulation. It has been found that such electro-stimulation has various beneficial effects, notably pain is substantially relieved. It has also been found that local electro-stimulation activates growth of muscular tissue and activates the healing of wounds. Furthermore, electro-stimulation is employed as an alternative to traditional acupuncture. In order to achieve optimum beneficial effects, the electrical signals are to be applied to particular, optimum positions on the person's skin. It is known that these optimum positions locally have a minimum electrical impedance.

Such an electro-stimulation apparatus is known from the abstract of the Soviet patent SU 1 219 086.

The cited abstract mentions that the person clasps the counter electrode in the palm of one hand and the electrode system is placed so that a number of electrode pads are in electrical contact with the person's skin. The cited abstract mentions that the resistance of the acupuncture point is comparatively low and that a current regulator sets the current for the acupuncture point search.

SUMMARY OF THE INVENTION

An object of the invention is to provide an electro-stimulation apparatus which is easier to use and can operate more accurately than the conventional electro-stimulation apparatus. A particular object of the invention is to provide an electro-stimulation apparatus with which the optimum position for electro-stimulation is more comfortably and more accurately found.

This object is achieved according to the invention by an electro-stimulation apparatus which is characterized in that the electrode pads and the counter electrode are assembled in an electrode unit.

Because the counter electrode and the electrode pads are assembled in a preferably compact electrode unit, the counter electrode is not situated far from the electrode pads. Hence, the electrical impedances between individual electrode pads and the counter electrode accurately represent the skin's local electrical impedance at the positions on the person's skin where the electrode pads are positioned. Preferably, the counter electrode and the multitude of electrode pads are integrated in the electrode unit. Notably, the counter electrode and the electrode pads cannot be readily detached from the electrode unit. Furthermore, the electro-stimulation apparatus according to the invention does not require a separate counter electrode. The electro-stimulation apparatus according to the invention is easier to use since the person using the electro-stimulation apparatus does not need to clasp the counter electrode in the palm of the hand. Moreover, the counter electrode is not a separate component of the electro-stimulation apparatus. Hence, the electro-stimulation apparatus according to the invention requires the manufacture and assembly of fewer separate components. In addition, there is no risk of loss of the counter electrode.

In order to determine the optimum position for electro-stimulation, the electrode system is placed on the person's skin. It has been found that there are various rather large regions on the person's skin which contain respective optimum electro-stimulation positions relating to particular ailments or disorders of the person. It appears that these regions have a diameter of from a few centimeters to some ten centimeters and that it is quite simple to indicate these regions for various ailments. In particular, among a huge number of examples, a region between the shoulder blades appears to be related to general fatigue, a region on the lower portion of the sternum appears to be related to asthmatic cough, and a region on the upper portion of the sternum appears to be related to bronchitis. When the electrode system is placed in the desired region on the person's skin, some of the electrode pads are activated so as to apply an electrical quantity, such as a voltage or an electrical current. Subsequently, the impedances at individual electrode pads are determined by measuring the difference between the electrical quantity applied at separate electrode pads and the counter electrode. In particular, the electrical potential difference between individual electrode pads and the counter electrode is measured or the electrical current passing between individual electrode pads and the counter electrode is measured. The electrode pad at which the impedance constitutes a local minimum is situated at or very close to the optimum position for electro-stimulation. The electro-stimulation can be applied through the same electrode pad as used to measure the impedance, but it is also possible to employ a separate stimulation electrode which is very close to or occupies substantially the same position as the electrode pad at which the impedance is locally minimum.

These and other aspects of the invention will be further elaborated with respect to the embodiments of an electro-stimulation apparatus according to the invention as defined in the dependent claims.

Various geometries of the arrangement of the electrode pads and the counter electrode are useful for integration in the electrode unit. In a particularly simple arrangement the counter electrode surrounds a part of or all of the electrode pads. The counter electrode is formed as a conducting loop; for example, the loop has a circular, oval or rectangular shape. A part of or all electrode pads are located within the loop. Because the arrangement is simple, it is easy and hence inexpensive to manufacture the integrated electrode unit. The counter electrode can also be positioned between individual electrode pads. For example, the counter electrode is formed as one or more conducting strips which are positioned between individual electrode pads, or the conducting strip(s) meander(s) between the individual electrode pads.

The counter electrode in another embodiment is formed as a plurality of counter electrode elements; in particular, a sink group of the electrode pads is employed as the counter electrode elements and a source group of the electrode pads is employed to apply the electrical quantity, such as the voltage or the electrical current, to the person's skin. The counter electrode elements, notably the electrode pads of the sink group, are maintained at the substantially constant reference voltage, for example, at ground potential. The distances between neighbouring counter electrode elements and electrode pads of the source group are substantially equally small throughout the electrode system. Hence, the electrical impedances between electrode pads of the source and the sink group accurately represent the local electrical skin impedance of the person. Usually, the size of the electrode system is about 2×2 cm, or 5×5 cm. As more electrode pads having smaller sizes are provided, the spatial resolution for measuring the local electrical impedance is increased and, consequently, the optimum position for electro-stimulation can be found more accurately. The more accurately electro-stimulation is performed at the optimum stimulation position, the more effective beneficiary effects are achieved.

The electrode pads and the counter electrode are part of the electrode system which is incorporated in an electronic circuit. Preferably, the electrode pads of the electrode system are incorporated in a matrix structured electronic circuit. For example, the electrode pads are arranged in a two-dimensional square or triangular pattern. Preferably, 8×8, 16×16 or 512×512 electrode pads are provided. A source conductor is provided to apply the first electrical quantity in the form of the voltage or the electrical current to electrode pads of the source group. A sink conductor is provided to receive the second electrical quantity in the form of the electrical current or the voltage from the electrode pads of the sink group. The second electrical quantity at the sink electrode pads is caused by applying the first electrical quantity to the source electrode pads so that the electrical impedance between source and sink electrode pads can be derived from the electrical quantity received from the sink electrode pads. Electrode pads in the sink and source groups will be designated as source and sink electrode pads, respectively. The source electrode pads and the sink electrode pads have the same construction and electrode pads are arranged in the source group by connecting them electrically to the source conductor so that the first electrical quantity can be applied to the source electrode pads. Similarly, electrode pads are arranged in the sink group by electrically connecting them to the sink conductor so that the second electrical quantity can be received from the sink electrode pads. The source electrodes are switchably coupled to the source conductor and the sink electrodes are switchably coupled to the sink conductor. Electrode pads are selected to apply or receive the voltage or the electrical current by closing relevant switching elements between said electrode pads and the source conductor or the sink conductor. Preferably, the switching elements are transistors, e.g. thin-film field effect transistors, which are controlled by applying addressing signals to the gate contacts of the transistors. The addressing signals are conveniently supplied over addressing lines which can be incorporated in the electronic circuit. By controlling appropriate switching elements, source electrode pads are selected to apply the first electrical quantity, for example to apply the voltage. By controlling appropriate switching elements sink electrode pads are selected to receive the second electrical quantity, for instance to receive the electrical current. The electrical impedances between source electrode pads and sink electrode pads are determined by measuring the electrical currents generated at the sink electrode pads and measuring the applied voltages at the source electrode pads, subsequently, the optimum stimulation position is found at the position of the sink electrode pad having the lowest electrical impedance with respect to the source electrode pads. It is also to be noted that the sink electrode pads function as the counter electrodes, but a separate counter electrode which is maintained at a constant reference voltage, for example at ground potential, can also be used.

Preferably, a source and a sink conductor share a common line conductor. The common line conductor is at option coupled to the source unit so as to function as the source conductor and coupled to the sink unit so as to function as the sink conductor. The electronic circuit has a comparatively simple architecture with a rather small number of lines. Preferably, there is provided a plurality of common line conductors which at option function as one or more of source conductors or as one or more sink conductors. When a plurality of common line conductors is employed it is simultaneously possible to supply the first electrical quantity and to receive the second electrical quantity from separate electrode pads of the source group and of the sink group, respectively In a more elaborate embodiment of the electronic circuit the electrical current is applied to electrode pads of an activation source group and the electric current is received from electrode pads of an activation sink group. Electrode pads of the activation group are switchably coupled to the source conductor or to the sink conductor. Electrode pads of the probe group are switchably coupled to a source voltage line or to a sink voltage line. Electrode pads in the activation and probe group, respectively are designated activation electrode pads and probe electrode pads, respectively. Activation electrode pads which are coupled to the source conductor or to the sink conductor are named activation source and activation sink pads, respectively. The electrical current flows from one or more electrode pads of the activation source group to one or more electrode pads of the activation sink group. Voltages are probed from electrode pads of a probe group. Thus, voltages at electrode pads of a probe group are measured at electrode pads of the probe group due to an electrical current flowing between electrode pads of the activation group. The voltages at the probe electrodes are caused by the current flowing between the activation electrode pads. Notably the measurement of voltages at electrode pads between which the electric current flows is avoided. In this set up the measurement of the voltages hardly influences the electrical current so that the voltages area measured reliably and accurately.

In a more simple circuit architecture the source voltage line and the drain voltage line are formed as a common voltage line. The common voltage line is switchably coupled to separate voltage probes so as to act at option as the source voltage line and the drain voltage line. Preferably, a plurality of common voltage lines is provided so that different voltages from separate probe electrode pads can be probed simultaneously. Electrode pads are selected for probing voltages by closing relevant switching elements between said electrode pads and the source voltage line or the drain voltage line. The electronic circuit having common voltage lines instead of separate source and drain voltage lines has a simple circuit lay-out because the number of conducting lines is comparatively small. Hence, such an electronic circuit can be more easily manufactured.

Advantageously, the electrode unit comprising the electrode pads and the counter electrode is provided on a flexible substrate. The electrode unit can then be easily placed on the person's body, for example, wrapped around an arm or leg. Preferably, the electrode unit on the flexible substrate is incorporated on an inflatable band which will help to accurately maintain the correct location during the electro-stimulation.

Additionally, the invention relates to an electronic circuit comprising a source group of electrode pads and a sink group of electrode pads with a source conductor for applying a first electrical quantity to the electrode pads of the source group and a sink conductor for receiving a second electrical quantity from the electrode pads of the sink group. A first group of switching elements couple individual electrode pads of the source group to the source conductor and a second group of switching elements couple individual electrode pads of the sink group to the sink conductor. This inventive electronic circuit is particularly useful when employed in an electro-stimulation apparatus as disclosed above.

These and other aspects of the invention will be elucidated by way of example with reference to the embodiments described hereinafter and with reference to the accompanying drawing, in which:

DESCRIPTION OF THE PREFERRED EMBODIMENTS

Figure 1:
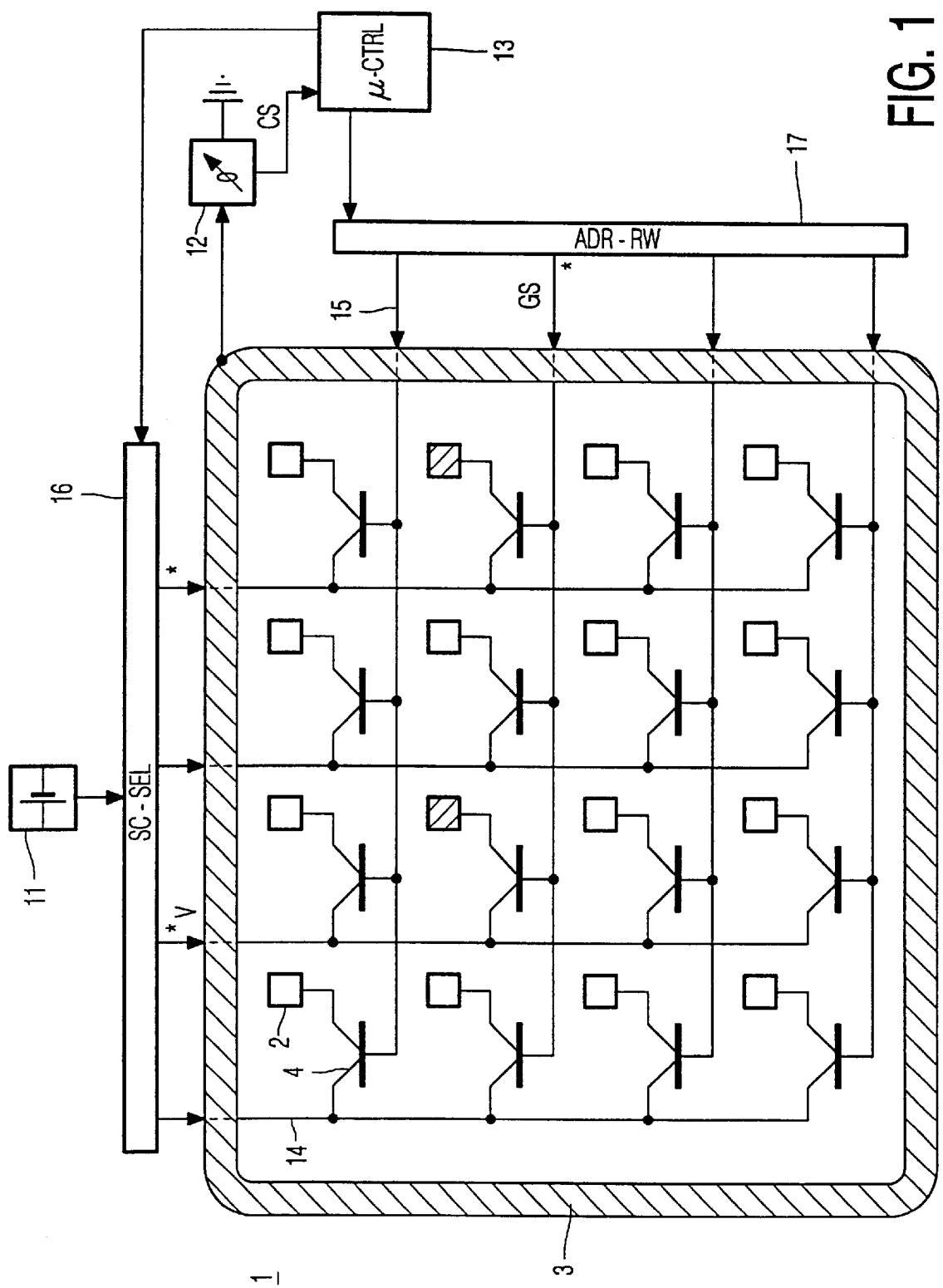
FIG. 1 is a schematic representation of a first embodiment of the electro-stimulation apparatus according to the invention.

FIG. 1 shows a schematic representation of a first embodiment of the electro-stimulation apparatus according to the invention. The electro-stimulation apparatus comprises an electrode system 1 which is placed on a person's skin such that most or all of the electrode pads 2 and the counter electrode 3 make electrical contact with the skin. One or more electrode pads 2 apply a voltage locally to the skin. The voltage is supplied by a voltage source 11 and as a consequence of the applied voltage an electrical current is received by the counter electrode 3. The electrical current is carried off to ground and is measured by a current meter, e.g. an ammeter. The current meter 12 generates a current signal (CS) whose signal level represents the measured current. The current signal is applied to a micro-controller 13.

Furthermore, the electrode system 1 includes voltage lines 14 and addressing lines 15. Preferably, the electrode pads 2 are configured in a square two-dimensional matrix. By way of example, a 4×4 matrix is shown, but in practice larger matrices such as 8×8 or 16×16 matrices can be employed. Such comparatively small matrices are advantageously manufactured from discrete electrical components mounted on a printed circuit board. The electrode pads can be mounted on one side of the printed circuit board and the conductor lines and switching elements are provided on the other side of the printed circuit board. Separate electrode pads 2 are coupled to one of the voltage lines 14 via respective switching elements, such a thin-film transistors 4. The source contact of each of the thin-film transistors 4 is coupled to the relevant voltage line 14 and the drain contact of each of the thin-film transistors 4 is coupled to the relevant electrode pad 2. The thin-film transistors 4 are coupled to respective addressing lines 15 via their gate contacts. Separate addressing lines 15 are coupled to thin-film transistors 4 in respective rows of the matrix. The electrode system also includes a source selection circuit 16 and a row addressing circuit 17 which are controlled by the micro-processor 13. The source selection circuit 16 applies the voltage (V) to one or more selected voltage lines 14. The row addressing circuit 17 applies gate signals (GS) to selected addressing lines 15. When a gate signal is applied to one of the addressing lines, the transistors coupled to that addressing line are closed, i.e. rendered conductive. Hence, the voltage is applied to electrode pads 2 which are coupled to a voltage line 14 that is activated and to an addressing line 15 that is activated. By way of example, activated voltage lines and activated addressing lines are marked with an asterisk (*) in the drawing.

The micro-controller 13, e.g. successively activates the voltage lines 14 and the addressing lines 15 so as to apply the voltage to successive electrode pads 2 or combinations of several electrode pads 2. The current meter 12 measures the electrical currents received from the counter electrode 3 and the current signals (CS) representing the electrical currents caused by applying the voltage to respective electrode pads are applied to the micro-controller 13. The micro-controller computes the skin impedance at the respective electrode pads, derives the local minimum of the skin impedance values, and selects the electrode pad at which the local minimum skin impedance occurs. Subsequently, the micro-controller activates the voltage line and the addressing line whereto the selected electrode pad, situated at or close to the position of minimum skin impedance is coupled. The selected electrode pad is then activated so as to apply a voltage to the skin at the optimum stimulation point, characterized by a locally minimum skin impedance, in order to perform an electro-acupuncture of transcutaneous electro nerve stimulation procedure. Notably, more than one local minimum skin impedance may be detected. In such a situation several electrode pads, each of them being situated at a locally minimum skin impedance, can be selected and the voltage can be applied to several optimum stimulation points.

In the embodiment shown in FIG. 1, the counter electrode 3 is arranged in the form of a more or less rectangular loop which surrounds the electrode pads 2. It is to be noted that the counter electrode 3 can also be arranged as a loop of a different shape, for example, a round loop. The counter electrode 3 may enclose all or a part of the electrode pads 2.

Figure 2:
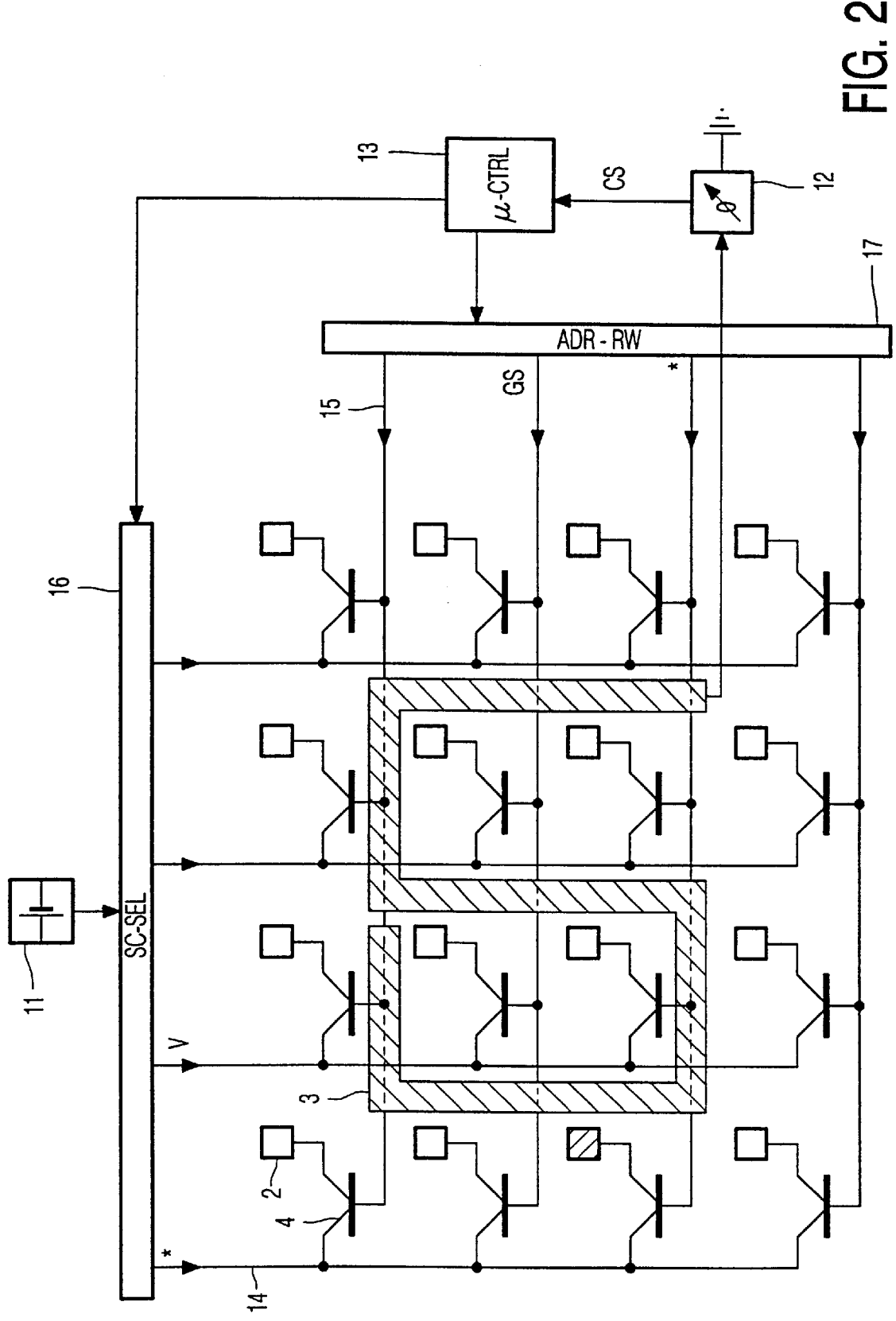
FIG. 2 is a schematic representation of a second embodiment of the electro-stimulation apparatus according to the invention.

FIG. 2 shows a schematic representation of a second embodiment of the electro-stimulation apparatus according to the invention. The counter electrode 3 in the embodiment shown in FIG. 2 is arranged as a conducting strip which meanders between the electrode pads 3. Although only a single meandering strip is shown in FIG. 2, in practice several counter electrodes may be provided between the electrode pads and/or one or more straight conductive strips may be used as counter electrodes.

The electrode pads and the counter electrode are preferably formed from an electrically conductive rubber. Such electrically conductive rubbers are easily integrated in electrically isolating rubber so as to form physically and electrically separated electrode pads. Moreover, electrically conductive rubbers are not poisonous.

Figure 3:
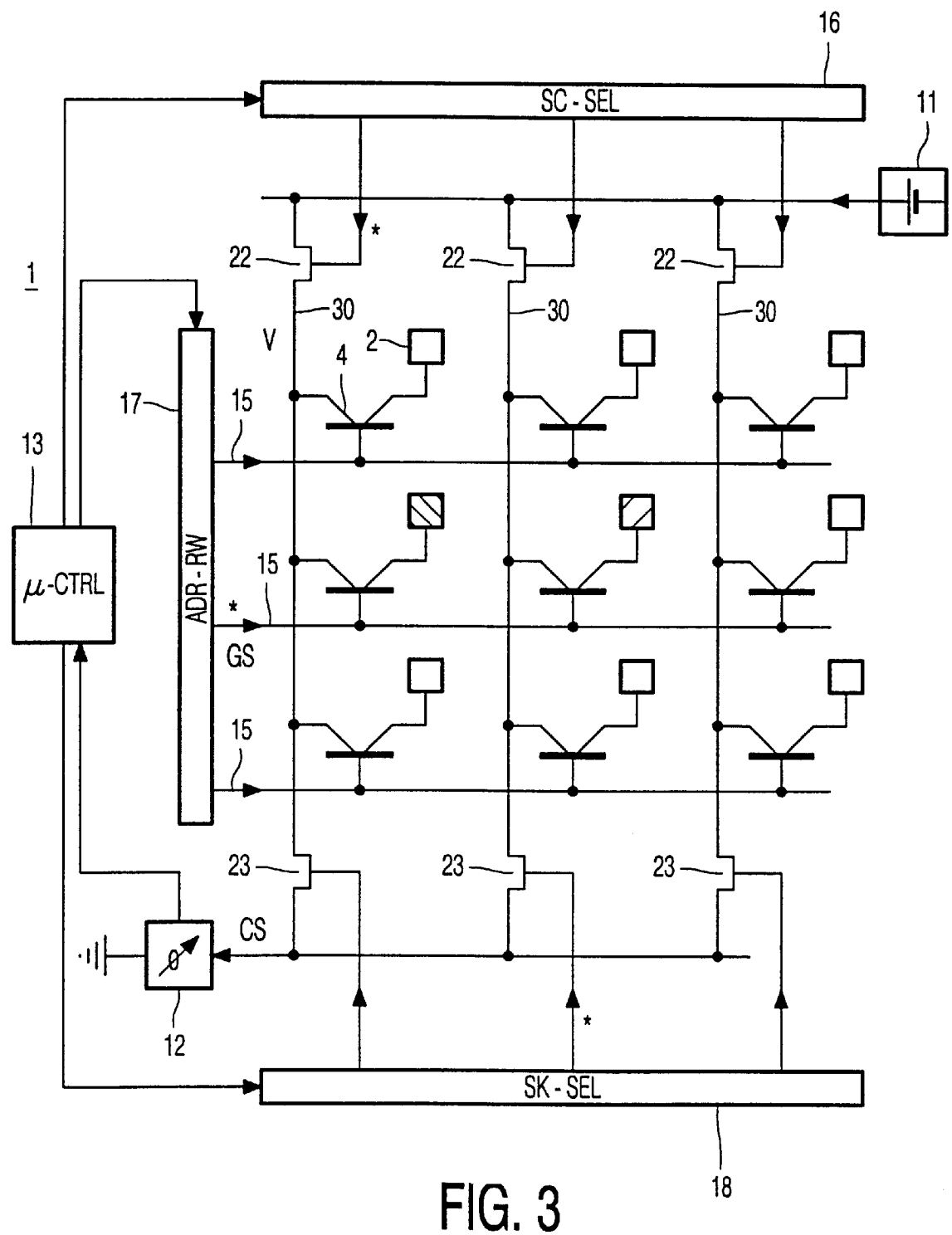
FIGS. 3,4 and 5 are schematic representations of embodiments of the electro-stimulation apparatus according to the invention in which advantageous electronic circuits are employed.

FIG. 3 is a schematic representation of an embodiment of the electro-stimulation apparatus according to the invention in which an advantageous electronic circuit is employed. The electronic circuit comprises a plurality of electrode pads 2. The electronic circuit comprises a number of common line conductors 30. Electrode pads 2 in one column of the matrix are coupled to the same common line conductor 30 by respective thin-film transistors 4. The common line conductors 30 are coupled to the voltage source 11 by switching elements, preferably transistors 22, which are controlled by a source selection circuit 16. The common line conductors 30 are also coupled to the current meter 12 by switching elements, preferably transistors 23, which are controlled by a sink selection circuit 18. The electronic circuit also includes a row addressing circuit 17 which is coupled to addressing lines 15. Separate addressing lines 15 are coupled to electrode pads 2 in the same row of the matrix. The addressing lines are coupled to the gate electrodes of the thin-film transistors 4. The row-addressing circuit 17 controls the thin-film transistors 4.

The source selection circuit 16 selects one or more common line conductors 30 to supply the voltage from the voltage source 11. To that end the relevant transistors 22 are closed so that the voltage is applied to the selected common line conductor 30. Such a selected common line conductor 30 then functions as the voltage line in the examples of the FIGS. 1 and 2 so as to apply the voltage to one or more electrode pads 2. The row addressing circuit 17 selects one or more rows of electrode pads 2 which are coupled to a common line conductor to which the voltage is applied. The row addressing circuit 17 applies a gate signal (GS) to the addressing line(s) 15 of the selected row(s) so as to close the thin-film transistors 4 in the selected row(s) so that the voltage is applied to the selected electrode pads 2.

The sink selection circuit 18 selects one or more common line conductors 30 to receive a current caused by the application of the voltage to one or more electrode pads 2. To that end, the relevant transistors 23 are closed so that the current received is led to the current meter 12. Such a selected common line conductor functions as a sink conductor which receives the electrical current caused by the applied voltage. The row addressing circuit selects one or more row electrode pads 2 which are coupled to a common line conductor which is electrically connected to the current meter so as to lead the electrical current to the current meter. The row addressing circuit applies a gate signal to the addressing line(s) of the selected row(s) so as to close the thin-film transistors 4 in the selected row(s) so that the voltage is applied to the selected electrode pads 2. The current meter generates a current signal (CS) which represents the electrical currents from electrode pads on common line conductors that are selected as sink conductors and are caused by voltages applied to electrode pads on common line conductors that are selected as source conductors. The current signals are generated for several selections of electrode pads and applied to the micro-controller. From the current signals the micro-controller computes the local minimum impedances which represent the optimum stimulation points.

Figure 4:
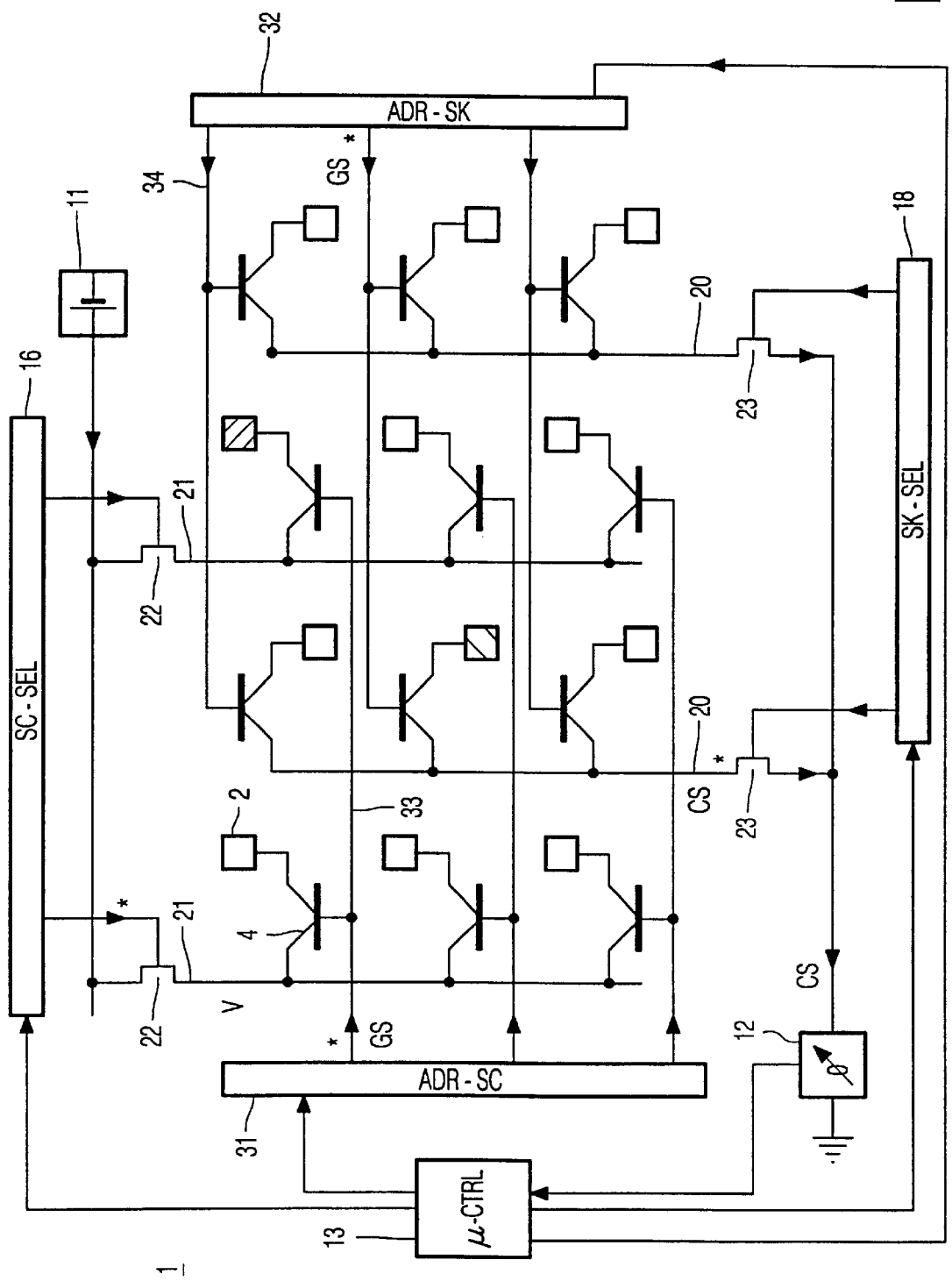

FIG. 4 shows a schematic representation of an embodiment of the electro-stimulation apparatus according to the invention in which another advantageous electronic circuit is employed. The electronic circuit comprises several separate sink conductors 20 and several separate source conductors 21. The sink conductors 20 are electrically coupled to the current meter 12 and the source conductors 21 are electrically coupled to the voltage source 11. The source conductors 21 are coupled to the voltage source 11 by switching elements, such as transistors 22 which are controlled by the source selection circuit 16. The electrode pads 2 that are switchably coupled to the voltage source 11 form one or more source groups. The sink conductors 20 are electrically coupled to the current meter 12 by switching elements 23, such as transistors, which are controlled by the sink selection circuit 18. The electrode pads 2 that are switchably coupled to the current meter 12 form one or more sink groups.

The electronic circuit also includes source addressing lines 33 and sink addressing lines 34. The source addressing lines 33 are coupled to the gate contacts of respective thin-film transistors 4 of electrode pads 2 that are coupled to one of the source conductors 21. The sink addressing lines 34 are coupled to the gate contacts of respective thin-film transistors 4 of electrode pads 2 that are coupled to one of the sink conductors 20. A source addressing circuit 31 is coupled to the source addressing lines 33 and a sink addressing circuit 32 is coupled to the sink addressing lines 34. By applying gate signals (GS) to source addressing lines 33, thin-film transistors 4 of the selected electrode pads 2 in the source group are selected for application of the voltage from the voltage source. By applying gate signals (GS) to sink addressing lines 34, thin-film transistors 4 of the selected electrode pads in the sink group are selected wherefrom the current caused by application of the voltage to electrode pads in the source group is measured. Electrode pads 2 in the source group and the sink group, respectively, can be present in different columns or in the same column of the matrix, because separate source and sink conductors are provided with separate sink addressing and source addressing circuits. Electrode pads to which the voltage is applied and from which the electrical current is received can be present in different rows or in the same row of the matrix, because separate sink and source addressing lines are provided. The micro-controller 13 controls the source and sink selection circuits 16,18 and the source and sink addressing circuits. The micro-controller also derives the local impedance minima from the current signal (CS) from the current meter.

Figure 5:
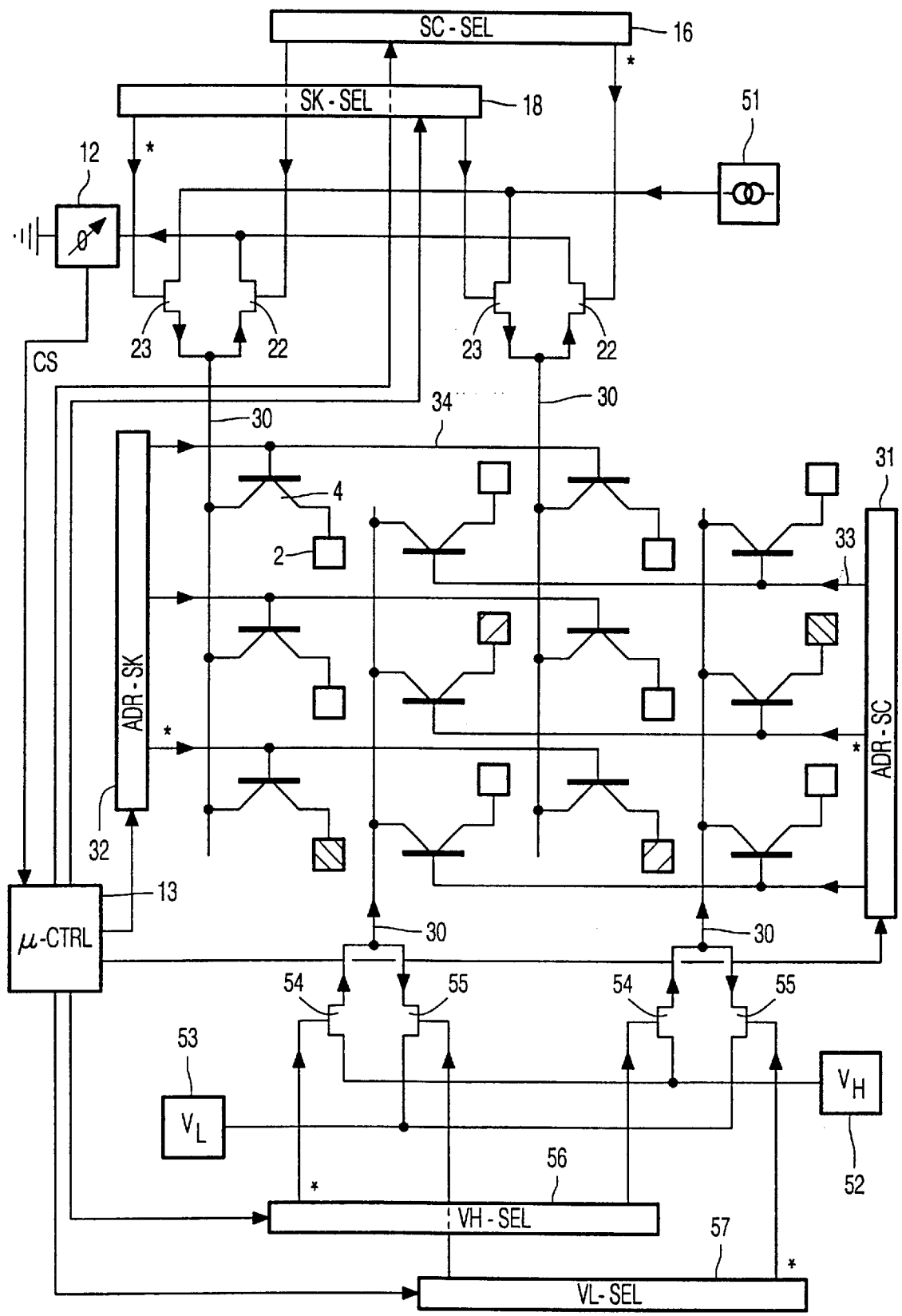

FIG. 5 shows a schematic representation of an embodiment of the electro-stimulation apparatus according to the invention in which another advantageous electronic circuit is employed. The electronic circuit shown in FIG. 5 is in particular arranged to perform four-point measurements. The electrode pads 2 are arranged in a matrix. The electronic circuit also comprises several common line conductors 30. Common line conductors 30 of a first group are switchably coupled to the current source 51 and to the current meter 12. The common line conductors of the first group are coupled to the current meter 12 and to the current source 51 by transistors 22,23. The transistors 22,23 are controlled by the source selection circuit 16 and the sink selection circuit 18. The common line conductors that are selected to be coupled to the high-voltage source function as activation source conductors. The common line conductors that are selected to be coupled to the low-voltage source function as activation sink conductors. Furthermore, the electronic circuit comprises a second group of common line conductors which are switchably coupled to a high-voltage source 52 and a low-voltage source 53. For example, use is made of a DC voltage of 40V, and an AC voltage of 25V at 400 Hz or 50V at 1.5 kHz. The common line conductors 30 of the second group are coupled to the high-voltage source 52 and the low-voltage source 53 by means of transistors 54,55. The transistors 54,55 are controlled by a high-voltage selection circuit 56 and a low-voltage selection circuit 57. The electronic circuit also includes source addressing lines 33 and sink addressing lines 34. The electrode pads 2 are coupled to separate common line conductors by means of respective thin-film transistors 4. The source and sink addressing circuits 31,32 apply gate signals via the source and sink addressing lines 33,34 so as to close thin-film transistors 4 whose gate contacts are coupled to the source and sink addressing lines. The gate signals close the relevant thin-film transistors 4 to connect electrode pads 2 electrically to the relevant common line conductors. The electrode pads that are switchably coupled to the high-voltage source 52 or to the low-voltage source 53 form the activation group. The common line conductors that are selected to be coupled to the high-voltage source and to the low-voltage source function as source voltage lines and drain voltage lines, respectively. The electrode pads 2 that are switchably connected to the current source 51 and the current meter 12 form the probe group. The electronic circuit shown in FIG. 5 is arranged to measure local impedances by means of a so-called four point measurement. To that end, under control of the high-voltage selection circuit 56 one or more separate common line conductors 30 are electrically connected to the high-voltage source 52 and, under control of the low-voltage selection circuit 57 one or more separate common line conductors are electrically connected to the low-voltage source 53. The source addressing circuit 31 selects electrode pads 2 to be electrically connected to their respective common line conductors. Thus, a high-voltage and a low-voltage are applied to electrode pads 2 that are coupled to the activated source addressing line 33. Furthermore, one or more separate common line conductors are coupled to the current source 51 under the control of the source selection circuit and one or more common line conductors are coupled to the current meter 12 under the control of the sink selection circuit 18. The sink addressing circuit 32 applies gate signals, via selected sink addressing lines 34, so as to close thin-film transistors whose gate contact is coupled to the respective sink addressing lines 34. Thus, the sink addressing circuit 32 selects electrode pads 2 whereto the electrical current is applied or wherefrom the electrical current is received from depending on the setting of the transistors 22,23. Hence, the current meter measures the electrical current that flows between two (or more) separate electrode pads in the probe group, while an electrical potential difference is maintained between two (or more) electrodes in the activation group. From the current signals the microcontroller computes the local minimum impedances which represent the optimum stimulation points.

What is claimed is:

1. An electro-stimulation apparatus comprising:
   an electrode system for measuring local electrical impedance including
      a multitude of electrode pads, and
      a separate counter electrode held at a reference voltage, wherein
         the electrode pads and the counter electrode are assembled into an electrode unit, and
         the counter electrode surrounds at least a part of the electrode pads.

2. An electro-stimulation apparatus comprising:
   an electrode system for measuring local electrical impedance including
      a multitude of electrode pads, and
      a separate counter electrode held at a reference voltage, wherein
         the electrode pads and the counter electrode are assembled into an electrode unit, and
         the counter electrode is positioned between individual electrode pads.

3. An electro-stimulation apparatus as claimed in claim 2, wherein
   the electro-stimulation apparatus includes a multitude of counter electrodes and
   groups of counter electrodes are positioned between groups of electrode pads.

4. An electro-stimulation apparatus comprising:
   an electronic system including;
   a source group of electrode pads and a sink group of electrode pads,
   a source conductor for applying a first electrical quantity to electrode pads of the source group,
   a sink conductor for receiving a second electrical quantity from electrode pads of the sink group,
   a first group of switching elements coupling individual electrode pads of the source group to said source conductor, and
   a second group of switching elements coupling individual electrode pads of the sink group to said sink conductor.

5. An electro-stimulation apparatus as claimed in claim 4, wherein
   said source conductor and said sink conductor are formed by a common line conductor,
   the common line conductor being switchably coupled to a source unit by the first group of switching elements and the common line conductor being switchably coupled to a sink unit by the second group of switching elements,
   the source unit being arranged to apply the first electrical quantity to the common line conductor, and
   the sink unit being arranged to receive the second electrical quantity from the common line conductor.

6. An electro-stimulation apparatus as claimed in claim 4, wherein
   the electronic system comprises:
      an activation group of electrode pads and a probe group of electrode pads,
      an activation source conductor and an activation sink conductor,
      a source voltage line and a drain voltage line,
      a first plurality of switching elements coupling individual electrode pads of the activation group to the activation source conductor,
      a second plurality of switching elements coupling individual electrode pads of the activation group to the activation sink conductor,
      individual electrode pads of the probe group being switchably coupled to the source voltage line, and
      individual electrode pads of the probe group being switchably coupled to the drain voltage line.

7. An electro-stimulation apparatus as claimed in claim 6, wherein
   said source voltage line and said drain voltage line comprise a common voltage line,
   the common voltage lines being switchably coupled to separate voltage probes.

8. An electro-stimulation apparatus as claimed in claim 6, wherein
   said source conductor and said sink conductor are formed by a common line conductor,
   the common line conductor is switchably coupled to a source unit and the common line conductor is switchably coupled to a sink unit,
   the source unit is arranged to apply the first electrical quantity to the common line conductor, and
   the sink unit is arranged to receive the second electrical quantity from the common line conductor.

9. An electronic circuit, comprising:
   a source group of electrode pads and a sink group of electrode pads,
   a source conductor for applying a first electrical quantity to electrode pads of the source group,
   a sink conductor for receiving a second electrical quantity from electrode pads of the sink group,
   a first group of switching elements coupling individual electrode pads of the source group to said source conductor, and a second group of switching elements coupling individual electrode pads of the sink group to said sink conductor.

10. An electro-stimulation apparatus as claimed in claim 1, wherein
the electrode unit is provided on a flexible substrate.

11. An electro-stimulation apparatus as claimed in claim 7, wherein
said source conductor and said sink conductor are formed by a common line conductor,
the common line conductor is switchably coupled to a source unit and the common line conductor is switchably coupled to a sink unit,
the source unit is arranged to apply the first electrical quantity to the common line conductor, and
the sink unit is arranged to receive the second electrical quantity from the common line conductor.

12. An electro-stimulation apparatus comprising:
an electrode unit including an electrode system for measuring local areas of electrical impedance on a body to be electrically stimulated, said electrode system including a plurality of electrode pads at least one of which is a counter electrode,
a flexible substrate which supports said electrode system,
first means for selectively coupling a plurality of the electrode pads to a source of electric energy, and
second means for coupling the at least one counter electrode of the plurality of electrode pads to a point of reference voltage and to a means for measuring a current received from selected electrode pads.

13. The electro-stimulation apparatus as claimed in claim 12 wherein said at least one counter electrode comprises a single counter electrode that encircles all of the remaining plurality of electrode pads.

14. The electro-stimulation apparatus as claimed in claim 12 wherein the at least one counter electrode has a serpentine configuration and is positioned so that it passes between individual ones of the plurality of electrode pads.

15. The electro-stimulation apparatus as claimed in claim 12 wherein said plurality of electrode pads is arranged in a matrix of columns and rows,
said first and second coupling means comprises;
a matrix of transistor switches arranged in columns and rows and coupled to respective electrode pads,
a matrix of a first and second plurality of common line conductors,
a first plurality of transistor switches coupling the first plurality of said common line conductors to said source of electric energy,
a second plurality of transistor switches coupling said first plurality of common line conductors to said current measuring means,
third means for coupling the matrix of transistor switches to said first plurality of common line conductors,
fourth means coupling control electrodes of said matrix of transistor switches to the second plurality of said common line conductors,
an address circuit coupled to the second plurality of common line conductors to operate selected transistors of the matrix of transistor switches,
a source selection circuit coupled to control electrodes of the first plurality of transistor switches to selectively operate said first plurality of transistor switches, and
a sink selection circuit coupled to control electrodes of the second plurality of transistor switches to selectively operate the second plurality of transistor switches, whereby operation of the address circuit, the source selection circuit and the sink selection circuit causes certain selected electrode pads to operate as a source group of electrode pads and certain other selected electrode pads to operate as a sink group of electrode pads.

16. The electro-stimulation apparatus as claimed in claim 15 wherein said first plurality of common line conductors are arranged in parallel columns associated with respective columns of said electrode pads, and
said second plurality of common line conductors are arranged in parallel rows interspersed with said electrode pads.

17. The electro-stimulation apparatus as claimed in claim 12 wherein said plurality of electrode pads is arranged in parallel lines,
said first and second coupling means comprises;
a first plurality of transistor switches arranged in parallel lines and coupled to respective electrode pads,
a plurality of parallel sink conductors and a plurality of parallel source conductors,
a second plurality of transistor switches coupling the sink conductors to the current measuring means,
a third plurality of transistor switches coupling the source conductors to said source of electric energy,
third means coupling given ones of the first plurality of transistor switches to the sink conductors and given other ones of the first plurality of transistor switches to the source conductors,
a plurality of source address lines coupled to control electrodes of respective transistors of the first plurality of transistor switches that are coupled to respective source conductors,
a plurality of sink address lines coupled to control electrodes of respective transistors of the first plurality of transistor switches that are coupled to respective sink conductors,
a source address circuit coupled to the source address lines, and
a sink address circuit coupled to the sink address lines.

18. The electro-stimulation apparatus as claimed in claim 12 wherein said plurality of electrode pads comprises a first plurality of counter electrodes positioned between a second plurality of said electrode pads.

19. The electronic circuit as claimed in claim 9 further comprising:
a third group of switching elements for coupling the source conductor to a source of the first electric quantity,
a fourth group of switching elements for coupling the sink conductor to receive the second electrical quantity, and
means for selectively addressing the third and fourth groups of switching elements.

20. The electro-stimulation apparatus as claimed in claim 12 wherein said plurality of electrode pads comprises a single electrode unit including the flexible substrate.

21. The electro-stimulation apparatus as claimed in claim 20 wherein said first and second coupling means are a part of said single electrode unit.

22. The electro-stimulation apparatus as claimed in claim 2 which comprises a single counter electrode that is positioned between a plurality of electrode pads.

* * * * *